United States Patent
Bashirullah

(10) Patent No.: US 11,844,952 B2
(45) Date of Patent: Dec. 19, 2023

(54) SYSTEM FOR WIRELESSLY COUPLING IN VIVO

(71) Applicant: Galvani Bioelectronics Limited, Middlesex (GB)

(72) Inventor: Rizwan Bashirullah, Research Triangle Park, NC (US)

(73) Assignee: Galvani Bioelectronics Limited, Middlesex (GB)

( * ) Notice: Subject to any disclaimer, the term of this patent is extended or adjusted under 35 U.S.C. 154(b) by 204 days.

(21) Appl. No.: 17/164,350

(22) Filed: Feb. 1, 2021

(65) Prior Publication Data
US 2021/0154485 A1 May 27, 2021

Related U.S. Application Data

(63) Continuation of application No. 15/803,405, filed on Nov. 3, 2017, now Pat. No. 10,933,248.
(Continued)

(51) Int. Cl.
*A61N 1/372* (2006.01)
*A61N 1/378* (2006.01)
(Continued)

(52) U.S. Cl.
CPC .......... *A61N 1/3787* (2013.01); *A61B 5/0026* (2013.01); *A61B 5/0031* (2013.01);
(Continued)

(58) Field of Classification Search
None
See application file for complete search history.

(56) References Cited

U.S. PATENT DOCUMENTS

| 4,275,739 A | 6/1981 | Fischell |
| 5,358,514 A | 10/1994 | Schulman et al. |

(Continued)

FOREIGN PATENT DOCUMENTS

EP 2498196 A2 9/2012

OTHER PUBLICATIONS

International Patent Application No. PCT/US2017/059945; Int'l Written Opinion and the Search Report; dated Dec. 27, 2017; 8 pages.
(Continued)

*Primary Examiner* — Kennedy Schaetzle
(74) *Attorney, Agent, or Firm* — Merchant & Gould P.C.

(57) ABSTRACT

Implantable systems are described that include a stimulation device positionable in vivo and configured to communicatively couple to electrodes configured to stimulate or block body tissue and an auxiliary device positionable in vivo and including one or more coils configured to wirelessly couple, in vivo, to the stimulation device and to wirelessly couple to an ex vivo device. The auxiliary device may include a coil driver and a power source controlled by a processor and memory for storing data instructions for the coil driver and for storing data received from the stimulation device. The auxiliary device may also include a radio transceiver and an antenna. The stimulation device may include a housing, a coil, a power source and an integrated circuit for controlling the electrodes. The stimulation device may be coupled to a cuff via a lead and physically coupled to the auxiliary device.

17 Claims, 8 Drawing Sheets

Related U.S. Application Data

(60) Provisional application No. 62/417,423, filed on Nov. 4, 2016.

(51) Int. Cl.
    *A61N 1/36*    (2006.01)
    *A61N 1/05*    (2006.01)
    *H04B 5/00*    (2006.01)
    *A61N 1/375*   (2006.01)
    *A61B 5/00*    (2006.01)

(52) U.S. Cl.
    CPC ......... *A61N 1/0556* (2013.01); *A61N 1/3605* (2013.01); *A61N 1/375* (2013.01); *A61N 1/3754* (2013.01); *A61N 1/3756* (2013.01); *A61N 1/37223* (2013.01); *H04B 5/0081* (2013.01); *A61B 2560/0219* (2013.01); *A61M 2205/3538* (2013.01); *A61M 2205/3569* (2013.01); *H04B 5/0075* (2013.01)

(56) References Cited

U.S. PATENT DOCUMENTS

| | | | |
|---|---|---|---|
| 5,814,089 A | 9/1998 | Stokes et al. | |
| 6,141,588 A | 10/2000 | Cox et al. | |
| 6,272,382 B1 * | 8/2001 | Faltys | A61N 1/375 607/57 |
| 6,366,815 B1 | 4/2002 | Haugland et al. | |
| 7,155,284 B1 | 12/2006 | Whitehurst et al. | |
| 8,712,549 B2 | 4/2014 | Zdeblick et al. | |
| 8,755,893 B2 | 6/2014 | Gross et al. | |
| 10,933,248 B2 * | 3/2021 | Bashirullah | A61N 1/3754 |
| 2004/0103906 A1 | 6/2004 | Schulman et al. | |
| 2004/0215049 A1 | 10/2004 | Zdeblick et al. | |
| 2005/0119716 A1 * | 6/2005 | McClure | A61N 1/3727 607/33 |
| 2005/0192644 A1 | 9/2005 | Boveja et al. | |
| 2008/0021504 A1 | 1/2008 | McCabe et al. | |
| 2008/0039904 A1 | 2/2008 | Bulkes et al. | |
| 2010/0241195 A1 | 9/2010 | Meadows et al. | |
| 2012/0265273 A1 | 10/2012 | Libbus et al. | |
| 2013/0331919 A1 | 12/2013 | Zhang et al. | |
| 2017/0326375 A1 * | 11/2017 | Mcdonald | G16H 40/63 |

OTHER PUBLICATIONS

International Patent Application No. PCT/US2017/059945; Int'l Preliminary Report on Patentability; dated May 16, 2019; 8 pages.
European Patent Application No. 17868174.8; Extended Search Report; dated Mar. 27, 2020; 19 pages.

* cited by examiner

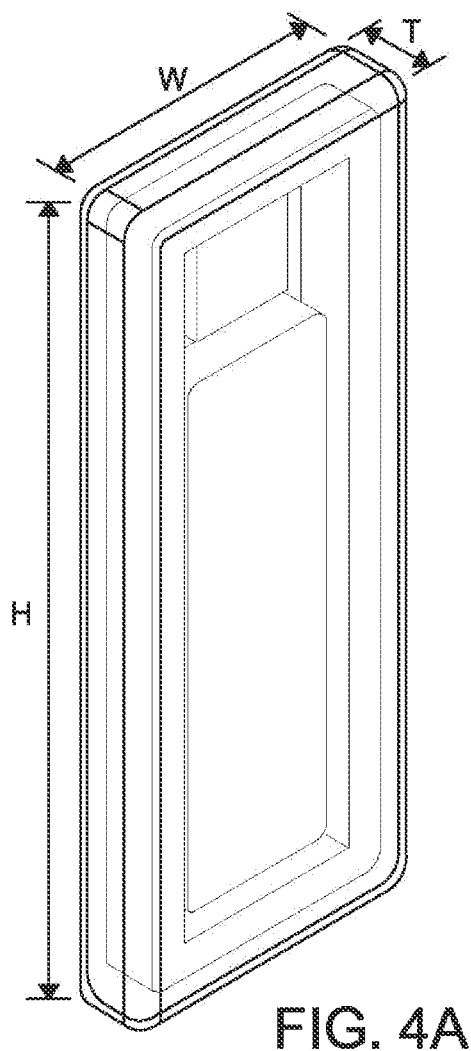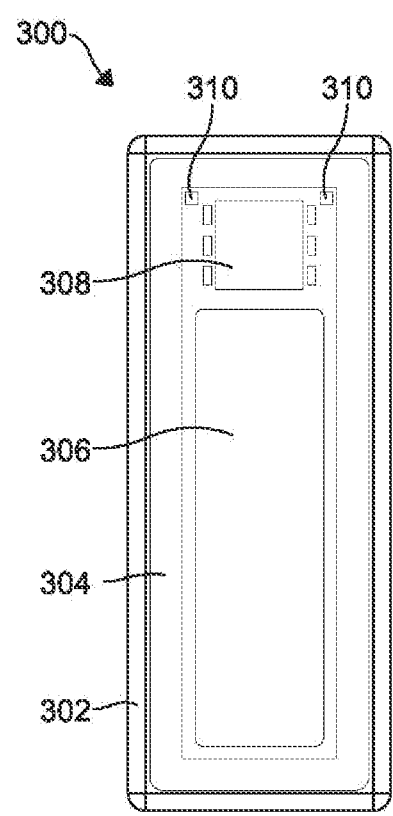
FIG. 4A
FIG. 4B

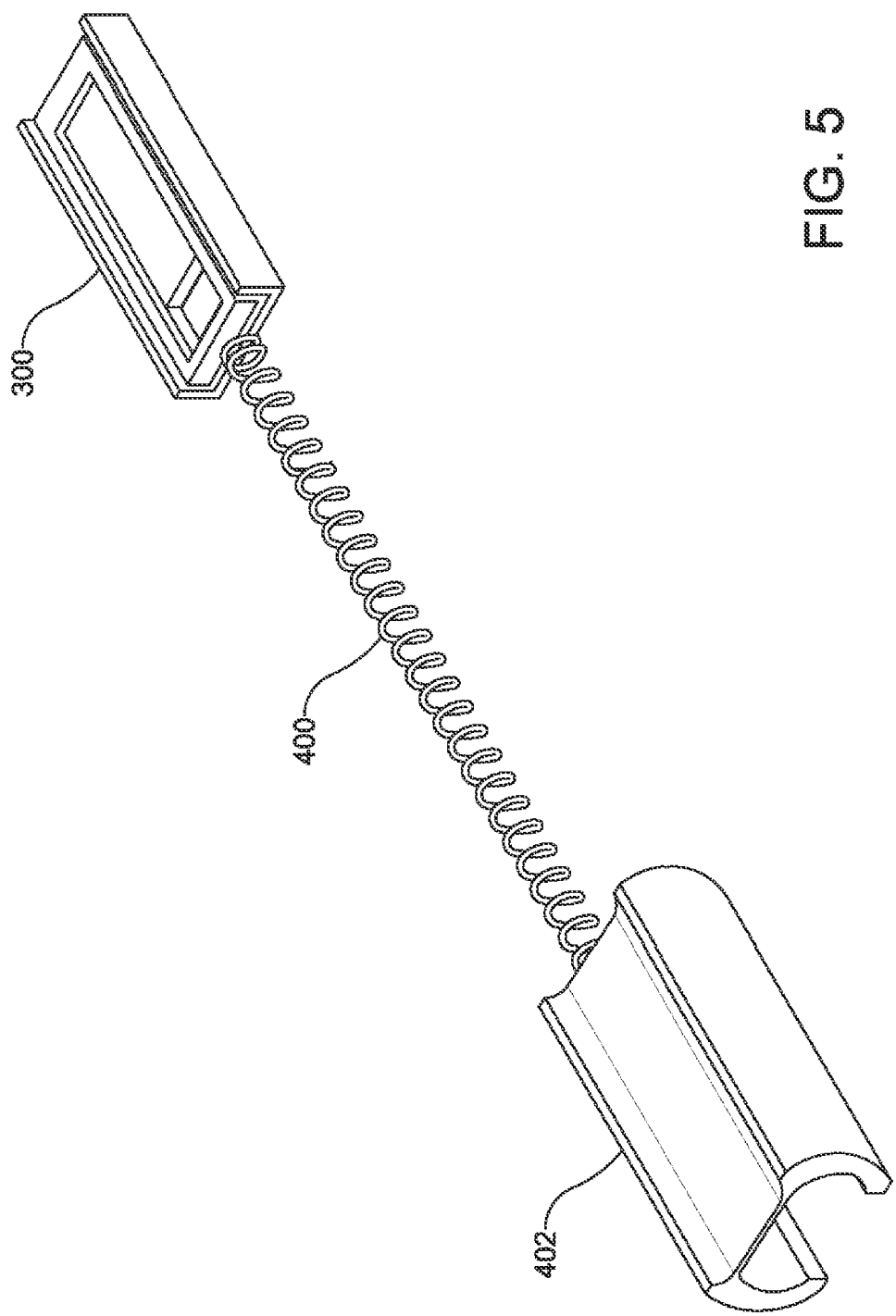

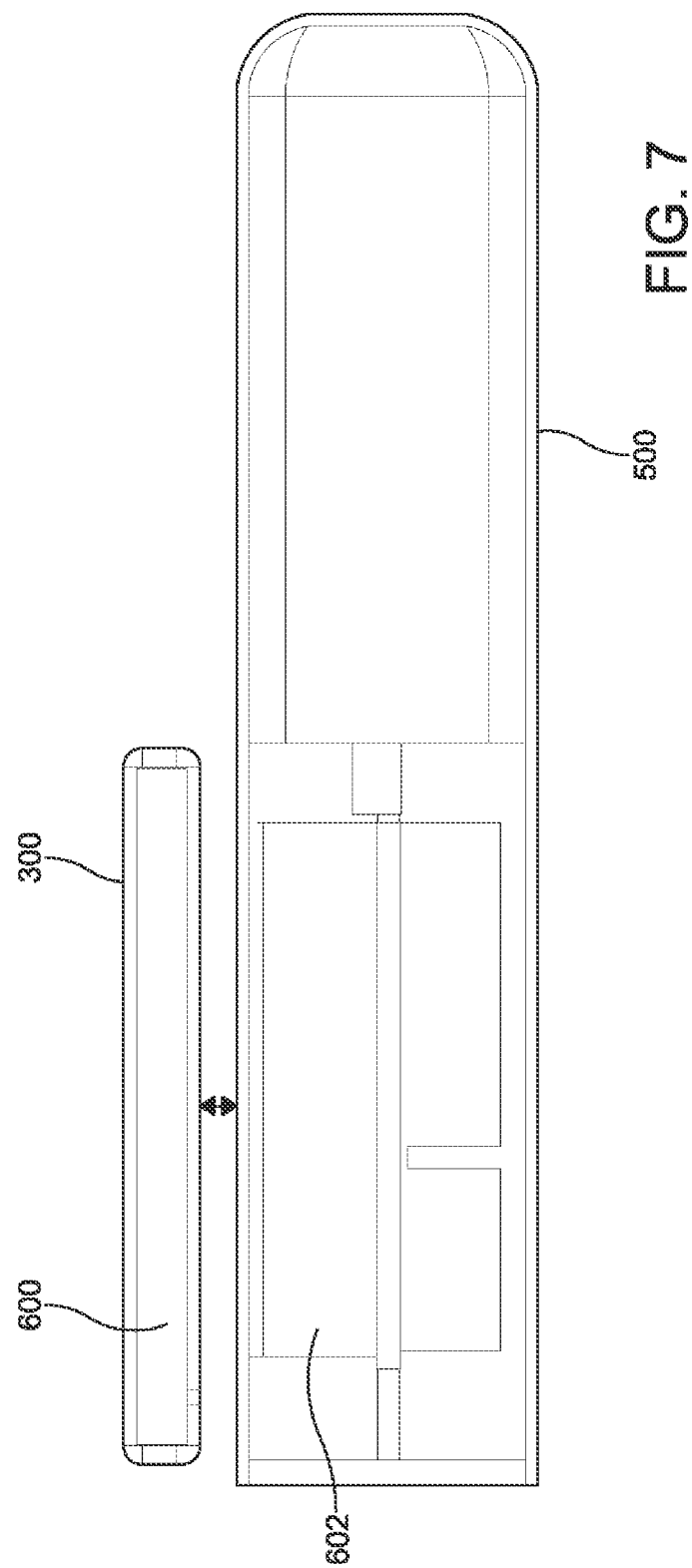

SYSTEM FOR WIRELESSLY COUPLING IN VIVO

CROSS REFERENCE TO RELATED APPLICATIONS

This application is a continuation of U.S. patent application Ser. No. 15/803,405, now issued as U.S. Pat. No. 10,933,248, filed Nov. 3, 2017; which claims benefit under 35 U.S.C. § 119(e) of Provisional U.S. Patent Application No. 62/417,423, filed Nov. 4, 2016; the contents of each of which are incorporated herein by reference in their entirety.

TECHNICAL FIELD

The present disclosure relates to in-vivo implantable devices, and more particularly, though not necessarily exclusively, to systems for wirelessly coupling between devices in vivo.

BACKGROUND

An in-vivo implantable device can be coupled to or include a lead with electrodes that are positioned to contact body tissue. The electrodes can sense information about the body tissue, source or sink current to cause an electrical change in the body tissue that can result in either a block or stimulation of physiological signals propagating in body tissue, or perform a combination of these or other functions. The electrodes can be communicatively coupled to a connector of the implantable device via wires to transfer data and electrical or magnetic energy. Each electrode can be communicatively coupled to a contact on the connector.

More electrodes for body tissue can result in better resolution for increased selectivity for recording and stimulation capabilities and options. The number of electrodes for body tissue, however, is limited due to size constraints on the implantable device limiting the number of connector contacts that can be physically included in the implantable device for the electrodes.

BRIEF DESCRIPTION OF THE DRAWINGS

FIG. 4A is a perspective view of a stimulation device according to one example.

FIG. 4B is a front view of the stimulation device according to one example.

FIG. 5 depicts an example of the stimulation device coupled via a lead to a cuff that includes electrodes according to one example.

FIG. 7 is a side view of the stimulation device and the auxiliary device from FIG. 6 according to one example.

DETAILED DESCRIPTION

Figure 1:
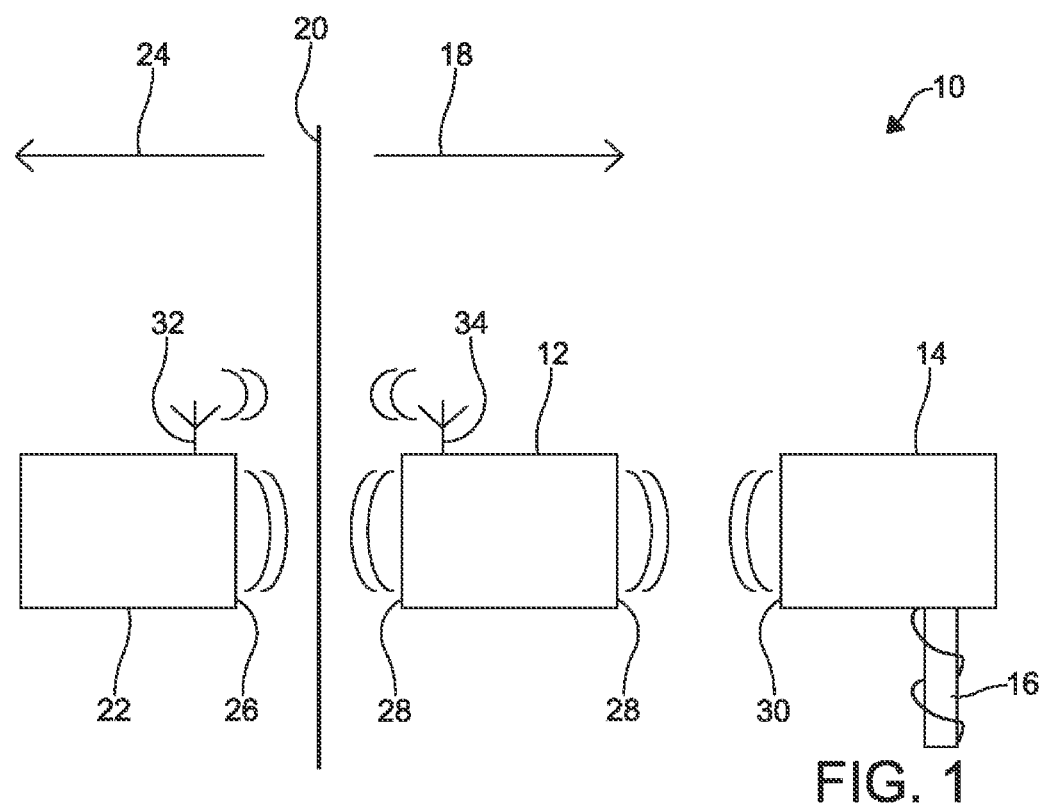
FIG. 1 is a block diagram of a system with components that can wirelessly couple in vivo according to one example.

Certain aspects and features relate to wirelessly coupling between devices in vivo. A stimulation device in vivo can include a coil that, through electromagnetic induction, can communicate with a coil of an auxiliary device in vivo. By wirelessly coupling between devices in vivo, components and functions can be split among more than one device and the stimulation device can have more space for interfacing with more electrodes for body tissue without increasing in size. For example, the stimulation device can output signals to electrodes to stimulate or block the body tissue and receive data about the body tissue detected by the electrodes.

The combination of outputting signals to stimulate or block body tissue, and record from body tissue, can be done in synchrony, in real-time, and in a closed-loop, to achieve improved treatment efficacy. Furthermore, stimulation through electrodes to source or sink current can cause an electrical change in the body tissue that can result in either a block or stimulation of physiological signals propagating in body tissue. Examples of body tissue include nervous tissue (for example, nerves of the central nervous system, nerves of the peripheral nervous system, autonomic nerves, somatic nerves, sympathetic nerves parasympathetic nerves, spinal nerves, cranial nerves, thoracic nerves, lumbar nerves, sacral nerves, cranial nerves, motor nerves, and sensory nerves), connective tissue (for example, bones, fibrous connective tissue or blood vessels, which may be veins, arteries, or capillaries), epithelial tissue and muscle tissue (which can include muscle fibers). The term body tissue is intended to encompass organs, which may comprise one or more tissue types. Thus, stimulation through electrodes can cause signal block or signal stimulation (e.g., excitation), such as those of nerve signals propagating in nerves and fibers. The auxiliary device can provide commands to the stimulation device to control the timing and frequency of the signals and data acquisition functions, and it can also have a larger power source for providing power to the stimulation device without patient involvement.

In some examples, the auxiliary device can be removed from the body and the stimulation device can remain in the body. A new auxiliary device with additional functionality can then be implanted without disrupting the body tissue proximate to the electrodes coupled to the stimulation device. The new auxiliary device can output commands and power to the stimulation device wirelessly. In other examples, the auxiliary device can be removed (or not implanted) and the stimulation device can wirelessly couple with an ex vivo device, which may be a wearable device.

The stimulation device can be part of an implant medical device (IMD) architecture for neuromodulation systems with an integrated circuit in a housing at a proximal end and electrodes (or body tissue contacts) at the distal end and configured into a cuff or other shapes, or included on a lead, depending on the target intervention point in vivo. The stimulation device can be relatively small in comparison to traditional IMDs, with a cross-sectional dimension of some examples being the same as, or similar to, that of a lead. A stimulation device can be hermetically encapsulated within a biocompatible ceramic or glass casing having electrical feedthroughs to interface to the external lead and electrodes (or contacts). The stimulation device can be any shape, such as rectangular, cylindrical, or a combination of these and other shapes for being integrated within a lead assembly and compatible with the desired anatomical target intervention site.

In some examples, the stimulation device can communicatively couple to electrodes on the lead wirelessly. For example, the stimulation device can generate a stimulation signal (e.g., an alternating current signal in a range of 20 kHz to 50 kHz) and the electrodes can be in the form of one or more coils that magnetically, and wirelessly, couple to an internal coil of the stimulation device to form a resonant network. For example, the number of electrodes may be two since a coil has two ends, to either stimulate or block the physiological signals propagating in the body tissue. A feedthrough interface may not be necessary in these examples, which may improve reliability of the implantable device.

A stimulation device according to some examples can include an integrated circuit, such as at least one application-specific integrated circuit (ASIC), and may include a battery. The integrated circuit can perform various functions. Examples of functions include delivering electrical pulses and recording data from electrodes that form a neural interface with body tissue, receiving power from a magnetizing inductive field using an internal coil, regulating the supply voltage, charging the battery and monitoring its state of charge, and establishing a bi-directional telemetry link with an auxiliary device to exchange command functions and transfer data. The stimulation device can also include a coil for power and data telemetry. In some examples, the battery supplies power in the absence of a magnetizing field.

The coil within the stimulation device can be wirelessly coupled via induction to an external magnetizing coil to energize the stimulation device and supply power to charge the battery. Alternatively, the power extracted from the magnetizing field can be used to deliver therapy to the patient directly without charging the battery. In the absence of a sufficient magnetizing field, the battery can supply power to the implant device to deliver therapy.

The battery can be a smaller size than otherwise used in an IMD. As a result, the amount of energy that can be stored and supplied by the battery can be smaller than is normally used. Furthermore, since typical rechargeable batteries can be cycled only a limited number of times (for example, 500 to 2000 cycles), the total usable energy over the lifetime of the battery may not be sufficient to deliver therapy over the desired lifetime of the implant device. The auxiliary device can provide additional power to the stimulation device wirelessly through induction in the absence of a battery in the stimulation device or after the life of the battery in the stimulation device.

The stimulation device can be wirelessly coupled to the auxiliary device to accommodate patient therapy needs over a wide range of therapeutic energy levels without changing the components within stimulation device. In one example, the proximal end of the lead assembly that includes the stimulation device body and a lead, can be inserted into a connector or header affixed to the auxiliary device. The header of the auxiliary device can be made from insulating material, such as epoxy, and can be a mechanical receptacle to accept the proximal end of the lead assembly. Unlike bal-seal connectors that involve electrical contacts and silicone isolation rings to accommodate the individual lead terminals, contacts may not be necessary to establish a direct current path between the lead assembly and the receptacle. By eliminating the need for electrical terminals between the lead assembly and the auxiliary device, the header and receptacle can be significantly decreased in size.

The stimulation device and the auxiliary device can be wirelessly coupled by a near-field, proximity-based link. When the stimulation device and the auxiliary device are proximal to each other, by for example inserting the stimulation device (or part of the stimulation device) into the receptacle of the auxiliary device header, the stimulation device and the auxiliary device can be paired by establishing a wireless channel that enables bi-directional data transfer between the devices and powering of the stimulation device should a battery in the stimulation device need charging. In some examples, more than one stimulation device can be wirelessly coupled in vivo to an auxiliary device and each stimulation device can be addressed independently using unique digital identification numbering and data protocols.

An auxiliary device according to some examples can include a radio transceiver and an antenna to communicate with an ex vivo patient remote-device or clinician-remote device. The auxiliary device can also include a processor and a memory subsystem to process and store data, manage overall operation of the auxiliary device, and manage communication with external charger and with the stimulation device. One or more integrated circuits can be included to manage wireless powering, battery management and the proximity-based link between the auxiliary device and the stimulation device. The auxiliary device can also include a rechargeable battery to supply power to the implanted devices. In another example, the auxiliary device can, in addition to the stimulation device, include stimulation and data recording circuits and electrical feedthroughs to interface with additional electrodes proximate to body tissue.

The proximity link between the auxiliary device and the stimulation device can be implemented in a number of ways. Examples of ways include incorporating within the auxiliary device a high-efficiency transmitter, such as a class-E driver or a class-D amplifier, to magnetize a transmit coil that can be wirelessly coupled to a receive coil within the stimulation device. Telemetry data can be transmitted to the stimulation device by, for example, encoding information in the amplitude or the phase of the transmit carrier frequency. Similarly, telemetry data from the stimulation device to the auxiliary device can be transmitted by modulating the reflected impedance using load shift keying or other methods.

The proximity link between the auxiliary device and the stimulation device can allow power supplied by the auxiliary device to power the stimulation device and to recharge the battery of the stimulation device. Power can be provided to the transmit inductor coil of the auxiliary device to generate an alternating current to magnetize the transmit inductor, and thereby generate magnetic flux lines that couple to the receiving coil in the stimulation device. The voltage induced by the magnetizing field can be rectified and regulated in a manner to ensure proper operation of the stimulation device, including charging the battery using constant current- and constant voltage-charging waveforms.

In another example, the transmit inductor coil can be positioned inside the header of the auxiliary device to increase the coupling strength between the transmit coil and the receiving coil and improve the overall power link efficiency between the auxiliary device and the stimulation device. A single auxiliary device can be wirelessly coupled to multiple stimulation devices by having the transmit coil or coils of the auxiliary device enclose an area that spans the size of the receive coils of the multiple stimulation devices. For example, a transmit coil can be incorporated inside a header receptacle that can receive the stimulation devices.

In another example, a single coil in the auxiliary device can be used for both transmitting power to the stimulation device and receiving power from an external charger that is an ex vivo device. In a similar configuration, the coil of the auxiliary device can be made to resonate strongly with the stimulation device to increase the overall efficiency of the power link between an external charger and the implant devices. This strongly coupled resonance effect can be used to improve wireless charging efficiency between the external charger and the auxiliary device or between the external charger and the stimulation device, enabling direct charging of the stimulation device from an ex vivo power source.

In some examples, the stimulation device can be coupled to an integral cuff. The cuff can be coupled directly onto an artery, vein, or nerve, for example a peripheral nerve, without a lead between the stimulation device and cuff. Power can be supplied by a stimulation device battery, or directly by an external energizing field coupled to the stimulation device coil.

Using various examples of the present disclosure can enable an implantable system to accommodate different target intervention sites, nerve/electrode interfaces, and therapeutic energy delivery needs for stimulation and blocking. For example, a unibody stimulation device with an integral cuff can allow the stimulation device to directly couple to an artery, vein, or nerve, for example a peripheral nerve, where the energy supplied by an implant during therapy is generally considered low. The same stimulation device can alternatively be integrated within a short lead assembly when leads are used to transition from a very small neural interface to the slightly larger lead assembly. The same stimulation device can be seamlessly paired with an auxiliary device using wireless coupling techniques, without changing the lead configuration. This arrangement can be used when the therapeutic energy requirement exceeds the amount of energy that can be supplied by a power source within the stimulation device. In some examples, an implant device with a larger energy source (e.g., in the auxiliary device) can be used to ensure therapy is delivered without depending on patient compliance.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure. The various figures described below depict examples of implementations for the present disclosure, but should not be used to limit the present disclosure.

FIG. 1 is a block diagram of a system 10 with components that can wirelessly couple in vivo according to one example. The system 10 includes an auxiliary device 12 and a stimulation device 14 that is coupled to a lead with electrodes 16. Both the auxiliary device 12 and the stimulation device 14 are positioned on the in vivo side 18 of body tissue 20 where the electrodes of the stimulation device 14 can be positioned to make physical contact with internal body tissue 20. The system also includes an ex vivo device 22 that is positioned on the ex vivo side 24 of the body tissue 20. The ex vivo device 22 can wirelessly couple to the auxiliary device 12 via coils 26 and 28, respectively.

The auxiliary device 12 can include one or more coils 28 for wirelessly coupling to the ex vivo device 22 and to the stimulation device 14. For example, the auxiliary device 12 can provide power and commands to the stimulation device 14, which includes coils 30, by wirelessly coupling to the stimulation device 14 in vivo. The stimulation device 14 can stimulate or block body tissue 20, gather information about the body tissue from the electrodes, or perform other functions. The auxiliary device 12 and the ex vivo device 22 can include antennas 32 and 34, respectively, for communicating information and commands via radio frequency signals, in addition to or instead of the wireless induction coupling link.

In other examples, the stimulation device 14, while also being capable of communicating via wireless coupling with the auxiliary device 12, can wirelessly couple directly to the ex vivo device 22, and the auxiliary device 12 may not be present. In some examples, the stimulation device 14 includes a radio transceiver and an antenna (not shown) for communicating with the ex vivo device 22 in addition to, or instead of, communicating via inductive coupling with the ex vivo device 22. In addition, the presence of both the stimulation device 14 and the auxiliary device 12, each with coils 28 and 30 having a resonant frequency, can cause an amplification effect to the wireless coupling with the ex vivo device 22 and improve power and communication transfer with the ex vivo device 22.

Figure 2:
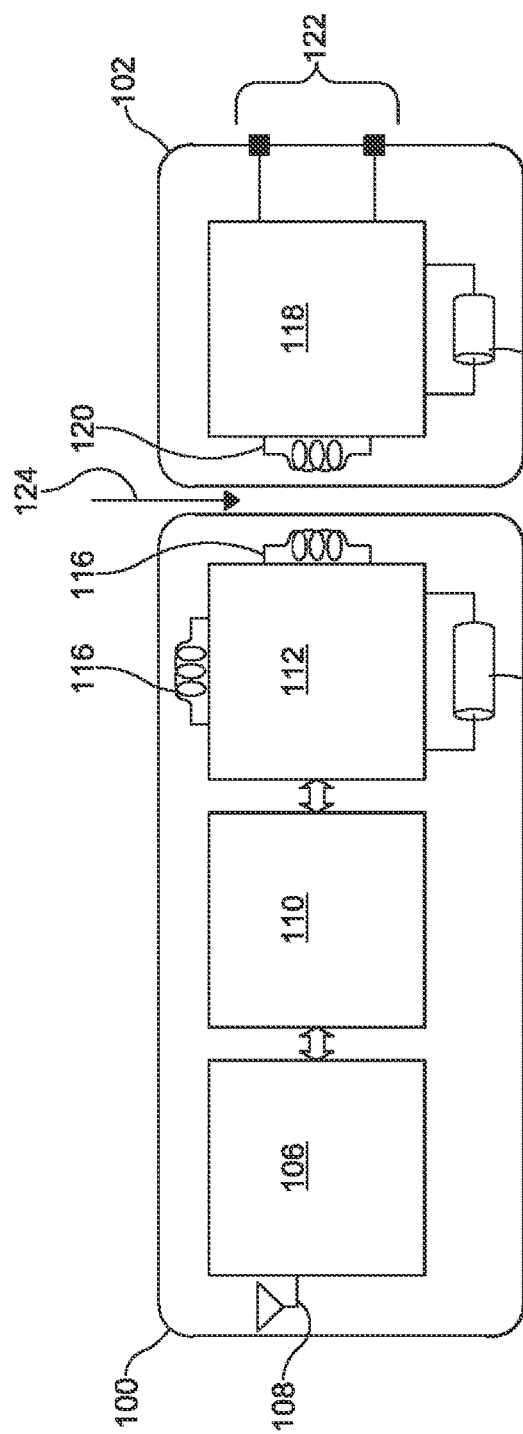
FIG. 2 is a block diagram of an auxiliary device and a stimulation device of an implantable system according to one example.

FIG. 2 is a block diagram of an auxiliary device 100 and a stimulation device 102 of an implantable system according to one example. The auxiliary device 100 includes a radio transceiver 106 in communication with an antenna 108, a processor and a memory 110, and a coil driver 112 for outputting high voltage power wirelessly. The coil driver 112 is coupled to a power source that is a battery 114 and one or more coils 116 for wirelessly coupling with an ex vivo device (shown in FIG. 1) and the stimulation device 102. Two coils 116 are shown in FIG. 2, but any number of coils, including one, can be used.

The processor may execute instructions stored in the memory to perform certain operations of the auxiliary device. The processor may include a single processing device or multiple processing devices. Examples of the processor include a field-programmable gate array, an application-specific integrated circuit ("ASIC"), and a microprocessor. At least a portion of the memory may include a non-transitory computer-readable medium from which the processor can access and execute instructions of the memory. The computer-readable medium may include electrical, optical, magnetic, or other storage devices capable of providing the processor with computer-readable instructions or other program code. Examples of the computer-readable medium include flash memory, memory chips, read-only memory, random-access memory (such as ferroelectric random-access memory or phase change memory), an ASIC, a configured processor, and optical storage. The instructions may include processor-specific instructions generated by a compiler or an interpreter from code written in any suitable computer-programming language, including, for example, C, C++, C#, an assembly programming language, etc.

The instructions include one or more applications or other engines for instructing the processor to perform various functions. Examples of functions include receiving commands from signals received by the radio transceiver 106, outputting commands to the stimulation device 102 to stimulate or block the body tissue, storing data received from the stimulation device 102, and controlling power transfers to the stimulation device.

The stimulation device 102 includes an integrated circuit 118, one or more coils 120, and an electrode interface 122. One coil 120 for the stimulation device 102 is shown in FIG. 2, but any number of coils can be used. The coil 120 can wirelessly couple via a proximity link 124 to a coil 116 of the auxiliary device 100 to receive power or exchange data. The electrode interface 122 can allow the stimulation device 102 to communicatively couple to electrodes for body tissue to output stimulating or blocking electrical signals and receive data from the electrodes.

The integrated circuit 118 can perform various functions, such as providing high voltage stimulation, data recording, and managing wireless coupling, power and data transfers, and battery charging. Included in the stimulation device is a power source 126 (a battery in this embodiment), which can be charged by power transferred wirelessly from the auxiliary device 100. The battery 126 in the stimulation device 102 can be smaller than the battery 114 of the auxiliary device 100. In other examples, the stimulation device does not include a battery and is instead powered via wireless coupling by the auxiliary device or an ex vivo device.

Figure 3:
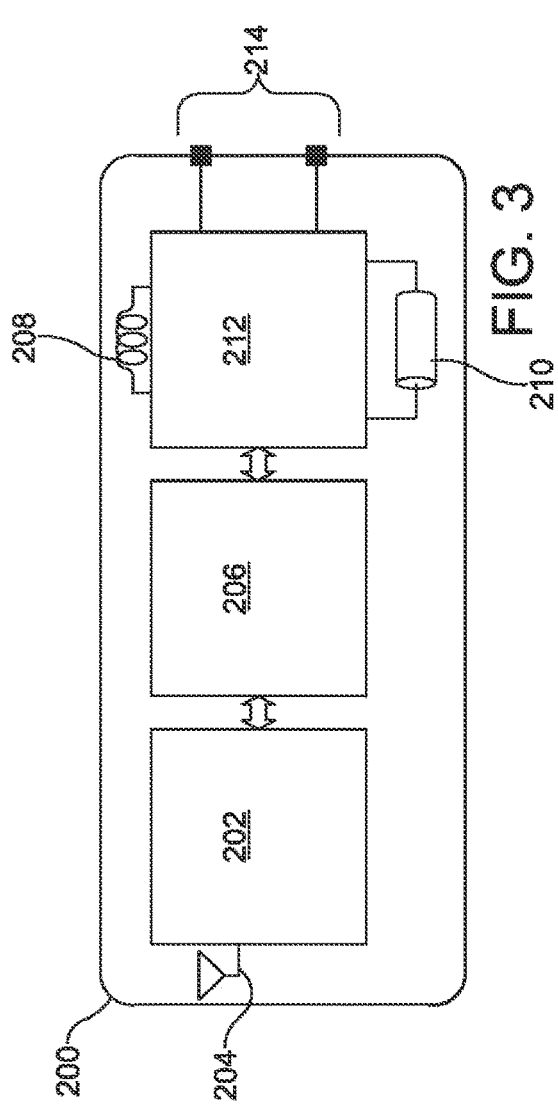
FIG. 3 is a block diagram of an auxiliary device according to another example.

FIG. 3 is a block diagram of an auxiliary device 200 according to another example. In addition to the radio frequency transceiver 202 and antenna 204, processor and memory 206, one or more coils 208, and power source 210, the auxiliary device 200 includes an integrated circuit 212 that is a coil receiver/driver and an electrode interface. The electrode interface can allow the auxiliary device to communicatively couple to electrodes 214 for body tissue. The integrated circuit 212 can control electrical signals provided to the electrodes 214 and receive data from the electrodes 214. The auxiliary device 200 can be used in addition to a stimulation device to provide a greater number of electrodes for body tissue.

FIGS. 4A and 4B show a stimulation device 300 according to some examples.

FIG. 4A is a perspective view of the stimulation device 300. FIG. 4B is a front view of the stimulation device 300. The stimulation device 300 in FIGS. 4A and 4B is rectangular-shaped with a height that is larger than a width. Along with a thickness, the height and width can be selected for a particular application and performance. A stimulation device according to other examples, however, can be shaped differently, such as by being shaped cylindrical.

The stimulation device 300 has a housing 302, which in this example is clear glass. An example of another type of housing is a ceramic housing. Within the housing are a coil 304, a power source 306 that is a battery, and an integrated circuit 308 that is an ASIC. The coil 304 can surround the battery 306 and the integrated circuit 308. In other examples, the stimulation device 300 does not include the battery, which can allow the package to be smaller.

The stimulation device 300 also has a contact interface that includes one or more feedthroughs 310, as seen in FIG. 4B. A feedthrough 310 can be an electrically conductive contact that can couple to a wire or other medium for communicatively coupling the integrated circuit to one or more electrodes for body tissue. The feedthrough 310 can extend through the housing 302 so that the wire or other medium can be coupled to it. By splitting functionality and components between the stimulation device 300 and an auxiliary device, the contact interface can be physically larger and include more contacts for communicatively coupling to more electrodes for body tissue.

FIG. 5 depicts an example of the stimulation device 300 coupled via a lead 400 to a cuff 402 that includes electrodes according to one example. The lead 400 can include a tube, cylinder, or other support structure around which is wrapped one or more wires to communicatively couple the stimulation device to electrodes included in the cuff 400. The cuff 400 can be sized for being placed proximate to body tissue, such as proximate to an artery, vein, or nerve, for example a peripheral nerve in the body. The cuff 400 can position the electrodes proximate to the body tissue to be treated or monitored. The wires can provide for bi-directional signal transfer so that electrical signals can be provided to the electrodes and data from the electrodes can be provided to the stimulation device 300.

The stimulation device 300 in FIG. 5 can be positioned at a distance with respect to an auxiliary device (shown in FIG. 6) such that the stimulation device 300 wirelessly couples, via coils, to an auxiliary device. The stimulation device 300 and the auxiliary device may be physically separated or the stimulation device 300 may physically contact the auxiliary device, but communicate via wireless coupling.

Figure 6:
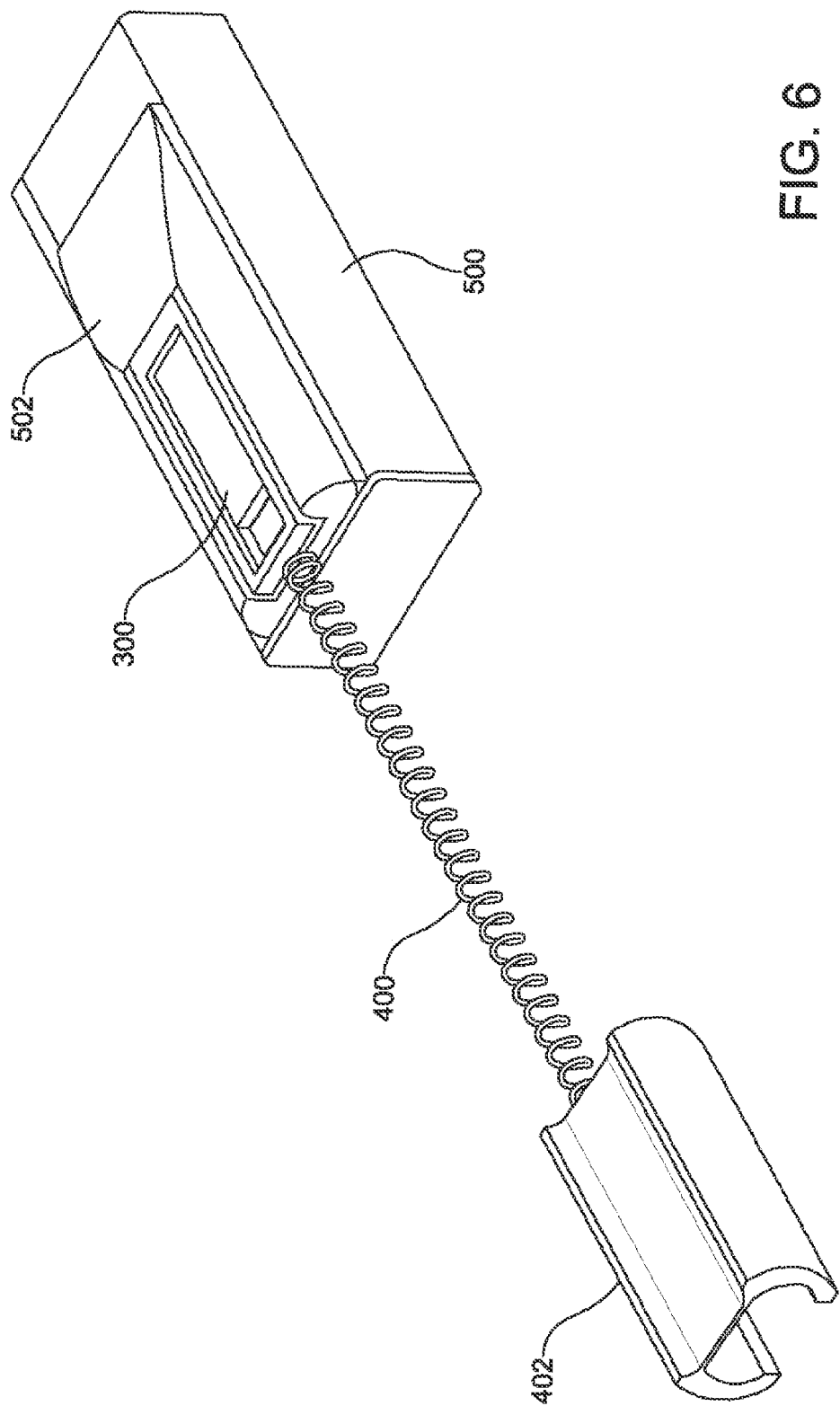
FIG. 6 is a perspective view of the stimulation device of FIG. 5 physically received in part of an auxiliary device according to one example.

FIG. 6 is a perspective view of the stimulation device 300 of FIG. 5 physically received in part of an auxiliary device 500 according to one example. The auxiliary device 500 includes a header 502 having a port that is shaped to receive and retain the stimulation device 300. The header 502 can be shaped similar to a cassette case such that the stimulation device 300 is removable via an intentional force, such as from a medical professional or from a tool, but not from unintentional forces, such as forces typically experienced by the devices in vivo. FIG. 7 is a side view of the stimulation device 300 and the auxiliary device 500 from FIG. 6, without the header 502 shown, according to one example. Although the stimulation device and the auxiliary device may be in physical contact, communication between the devices can be via a wireless coupling between the coil 600 of the stimulation device 300 and coil 602 of the auxiliary device 500, as shown by the double-headed arrow in FIG. 7.

Figure 8A:
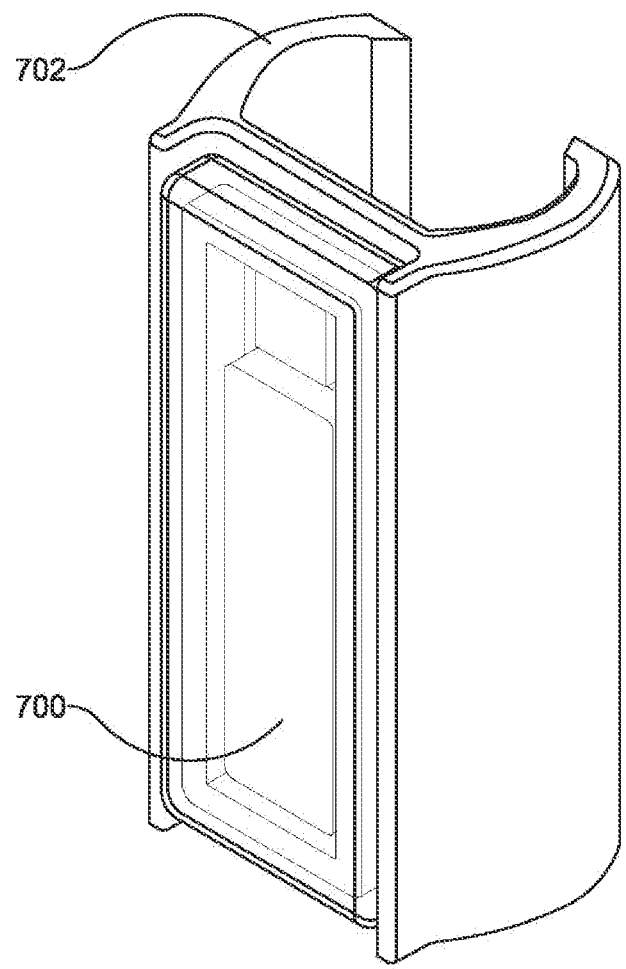
FIG. 8A is a perspective view of a stimulation device and a cuff according to one example.
Figure 8B:
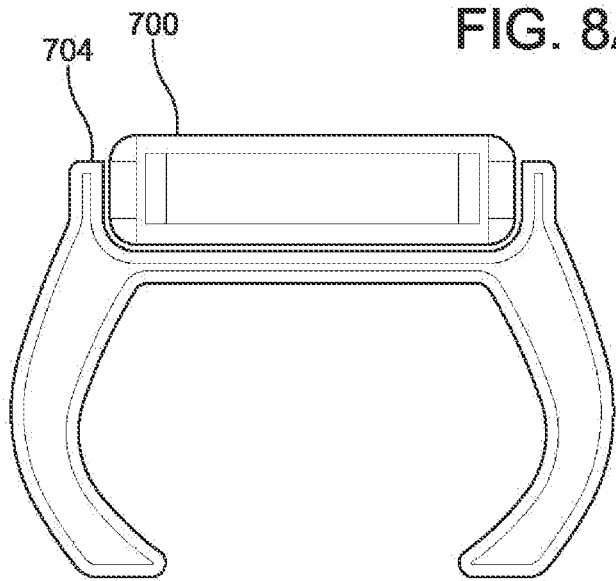
FIG. 8B is a side view of the stimulation device and the cuff of FIG. 8A according to one example.

FIGS. 8A and 8B depict a stimulation device 700 with a cuff 702 according to one example. The cuff 702 has a top portion 704 that is shaped to receive the stimulation device 700 to form a "unibody" design. The top portion 702 may also be shaped to retain the stimulation device 700 or an attachment mechanism can be used to retain the stimulation device 700 in the top portion 702. A contact interface of the stimulation device 700 can communicatively couple the stimulation device to electrodes without the use of a lead.

An implantable system according to some examples can allow for a high density of contacts for a stimulation device to allow for a greater number of electrodes. In some examples, a contact interface 800 can be made using semiconductor technology to increase the number and density of the contacts.

Figure 9:
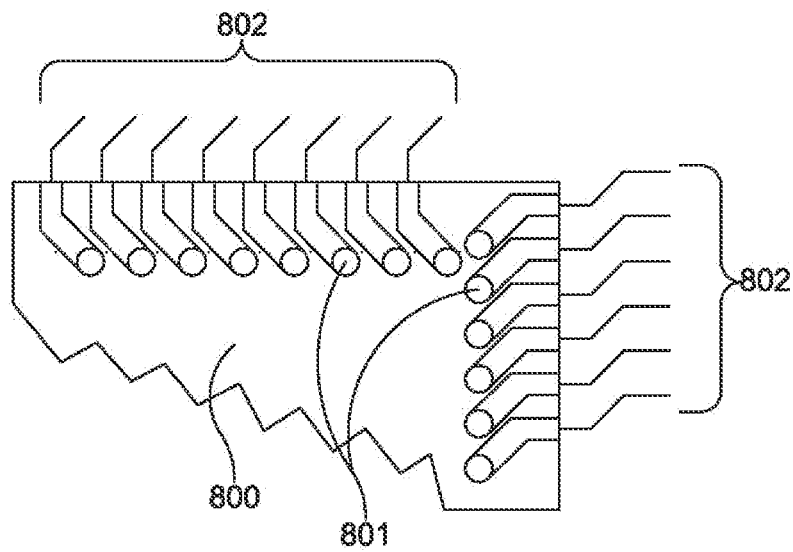
FIG. 9 depicts a partial top view of a contact interface for a stimulation device according to one example.

FIG. 9 depicts a partial view, cut away view of a contact interface 800 for a stimulation device according to some examples. The contact interface 800 includes a number of contacts 801 with conductive lines 802 coupling the contacts to wires or other mediums to electrodes (not shown). The contacts 801 and conductive lines 802 can be made via an etching semiconductor process or lithographic process compatible with planar semiconductor manufacturing to create the contacts and lines on a substrate in a precise manner. In other examples, the contacts 801 and conductive lines 802 can be created using laser energy to add or remove features on the substrate.

Figure 10:
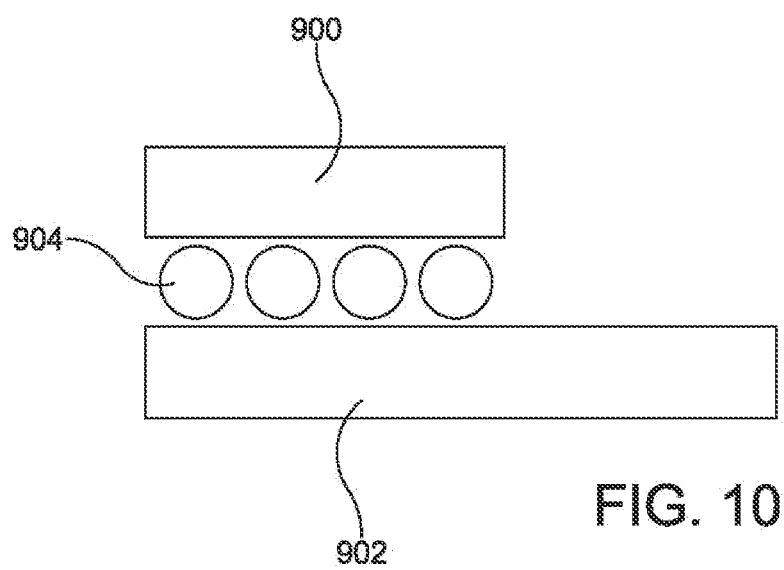
FIG. 10 depicts a side view of a contact interface coupled to another component according to one example.

FIG. 10 depicts a side view of an example of coupling the contact interface 900 to a lead wire 902 or medium via solder balls 904 so that the contacts of the contact interface are coupled to the wires in a flexible manner. In other examples, an epoxy or another physical coupling arrangement can be used to couple the contact interface to one or more lead wires.

Using an implantable system architecture according to some examples can provide flexibility in determining a physical footprint for the system in vivo. For example, a stimulation device can be used independent of an auxiliary device or with an auxiliary device, coupled to a lead with electrodes, coupled through a lead to a cuff with electrodes, coupled directly to the cuff, physically separated from the auxiliary device, or physically coupled to the auxiliary device.

The foregoing description of the examples, including illustrated examples, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts.

What is claimed:

1. An implantable system comprising:
   a stimulation device configured to communicatively couple to electrodes configured to stimulate or block body tissue, including one or more stimulation device coils; and
   an auxiliary device including one or more coils configured to wirelessly couple to the stimulation device and to wirelessly couple to a charger, wherein at least one coil of the auxiliary device is configured to resonate with at least one stimulation device coil to increase an efficiency of a power link between the stimulation device and the charger.

2. The implantable system of claim 1, wherein the stimulation device comprises:
   an integrated circuit configured to manage signal transfers through an interface to the electrodes; and
   the one or more stimulation device coils configured to wirelessly couple to the auxiliary device and configured to wirelessly couple to the charger.

3. The implantable system of claim 2, wherein the stimulation device comprises:
   a power source for the integrated circuit, the power source being rechargeable.

4. The implantable system of claim 2, wherein the auxiliary device comprises:
   a power source that is rechargeable by the charger through wireless coupling;
   a radio transceiver;
   an antenna for providing a wireless path for signals from the radio transceiver separate from wireless coupling;
   a processor; and
   a non-transitory computer readable medium on which instructions are stored, the instructions being executable by the processor to:
      receive commands from signals received by the radio transceiver;
      output commands to the stimulation device to stimulate or block the body tissue;
      store data received from the stimulation device; and
      control power transfers to the stimulation device.

5. The implantable system of claim 4, wherein the auxiliary device further comprises:
   an auxiliary device integrated circuit configured to manage signal transfers through an auxiliary device interface to additional electrodes configured to stimulate or block the body tissue.

6. The implantable system of claim 2, wherein the stimulation device includes the interface to the electrodes, the interface comprising one or more feedthroughs enabling wires connected to the electrodes to couple to stimulation device contacts in a housing of the stimulation device, the interface being formed using a laser or a lithographic process compatible with planar semiconductor manufacturing.

7. The implantable system of claim 1, further comprising:
   a cuff including the electrodes, the cuff being positionable proximate to an artery, vein, or nerve, in vivo,
   wherein the stimulation device is configured to couple to the cuff directly or indirectly.

8. The implantable system of claim 7, wherein the cuff comprises a top portion shaped to receive and retain the stimulation device.

9. The implantable system of claim 1, wherein the stimulation device is coupled to a lead that includes the electrodes.

10. An implantable device comprising:
    an integrated circuit configured to manage signal transfers through an interface to electrodes configured to stimulate or block body tissue; and
    one or more stimulation coils configured to:
       wirelessly couple to a charger, and
       wirelessly couple to an auxiliary device such that at least one of the one or more stimulation coils resonate with at least one auxiliary coil of the auxiliary device to increase an efficiency of a power link between the at least one stimulation coil and the charger.

11. The implantable device of claim 10, further comprising:
    a power source for the integrated circuit, the power source being rechargeable.

12. The implantable device of claim 10, further comprising a feedthrough configured to couple one or more wires connected to the electrodes to one or more stimulation device contacts in a housing of the implantable device, the interface being formed using a laser or a lithographic process compatible with planar semiconductor manufacturing.

13. The implantable device of claim 10, wherein the integrated circuit and the one or more coils are in a housing.

14. The implantable device of claim 13, further comprising:
    a cuff including the electrodes, the cuff being positionable proximate to an artery, vein, or nerve, In VIVO,
    wherein the housing is configured to couple to the cuff directly or indirectly through a lead.

15. The implantable device of claim 13, wherein the housing is coupled to a lead that includes the electrodes.

16. The implantable device of claim 10, wherein the auxiliary device is configured to wirelessly couple to the charger, the auxiliary device comprising:
    a processor; and
    a non-transitory computer readable medium on which instructions are stored, the instructions being executable by the processor for:
       outputting commands to the implantable device to stimulate or block the body tissue;
       store data received from the implantable device; and
       control power transfers to the implantable device.

17. An implantable system to monitor, stimulate, or block body tissue, comprising:
    a stimulation device configured to perform a first subset of two subsets of functions of the implantable; and
    an auxiliary device configured to perform a second subset of the two subsets of functions of the implantable system, the auxiliary device comprising one or more coils configured to wirelessly couple to the stimulation device and configured to wirelessly couple to a charger, wherein at least one coil of the auxiliary device is configured to resonate with the stimulation device to increase an efficiency of a power link between the stimulation device and the charger.

* * * * *